United States Patent [19]

Shepherd

[11] Patent Number: 4,977,516

[45] Date of Patent: Dec. 11, 1990

[54] DATA ACQUISITION DEVICE FOR BALANCING ROTATING COMPONENTS OF LARGE MACHINERY

[76] Inventor: James E. Shepherd, 3001 Charwood Pl., Raleigh, N.C. 27612

[21] Appl. No.: 393,850

[22] Filed: Aug. 14, 1989

Related U.S. Application Data

[63] Continuation of Ser. No. 37,010, Apr. 10, 1987, abandoned.

[51] Int. Cl.[5] .................... G01N 29/04; G01M 13/00
[52] U.S. Cl. .................... 364/508; 364/506; 364/550; 340/683; 73/570; 73/649; 73/660
[58] Field of Search ............... 364/505, 506, 508, 550, 364/494; 340/683; 73/570, 593, 649, 658, 660

[56] References Cited

U.S. PATENT DOCUMENTS

| 4,435,770 | 3/1984 | Shiohata et al. | 364/508 |
| 4,453,407 | 6/1984 | Sato et al. | 364/508 |
| 4,520,674 | 6/1984 | Canada et al. | 364/508 |
| 4,614,117 | 9/1986 | Taniguti | 364/508 |
| 4,683,542 | 7/1987 | Taniguti | 364/508 |
| 4,685,335 | 8/1987 | Sato et al. | 364/508 |

Primary Examiner—Parshotam S. Lall
Assistant Examiner—Brian M. Mattson
Attorney, Agent, or Firm—Rhodes, Coats & Bennett

[57] ABSTRACT

A device analyzes vibration-related problems in large rotating machinery which has the capability to receive input simultaneously from a plurality of vibration sensors. A microprocessor stores and processes the data collected, which is output as a value for the amplitude and phase of vibration at each location where a sensor is placed. The device includes communications capabilities which permit the collected data to be transmitted to a remote location for analysis.

5 Claims, 3 Drawing Sheets

DATA ACQUISITION DEVICE FOR BALANCING ROTATING COMPONENTS OF LARGE MACHINERY

This is a continuation of application Ser. No. 07/037,010 filed Apr. 10, 1987 now abandoned.

FIELD OF THE INVENTION

The present invention relates generally to the field of dynamic balancing of rotating machinery and more particularly to data acquisition devices for collecting, processing, printing and displaying data respecting vibration in a rotating shaft.

BACKGROUND OF THE INVENTION

Today, power generation plants are being designed for more demanding operating conditions, such as higher pressure and temperature conditions. These new designs create new balancing problems at a time when most power generation plants must operate at peak capacity with a minimum of downtime.

An increasing awareness of the negative effects of vibration on plant efficiency and reliability has led engineers to remove plants from service once vibration-related problems are detected in order to avoid more costly forced outages. These preventive maintenance programs require measurement of shaft vibration to test for abnormal dynamic operating conditions, such as unbalance.

Unbalance is the most common vibration related problem and causes stress in the rotor and its support structure which can result in (1) excessive wear of bearings, seals, couplings and gears; (2) fatigue failure of rotating components, such as shafts, blades and impellers; and (3) fatigue failure of stationary structures, such as bearing pedestals and stator frames. Correcting dynamic unbalance can increase plant efficiency and extend the useful life of power generation equipment.

Data acquistion devices are used in the industry to provide maintenance technicians and engineers with information needed to quickly and accurately balance rotating machinery on-site. Many of these devices are capable of receiving input on multiple input channels, but are capable only of acquiring data on a single input channel at any given time.

SUMMARY AND OBJECTS OF THE INVENTION

The invention is a data acquisition device used in connection with the balancing of large rotating machinery, such as gas and steam turbine-generators. The device has the capability to acquire, process, display, print and store data taken at up to twelve locations simultaneously. Communications capabilities are built into the data acquisition device which permits the collected data to be transmitted to a computer either locally or at a remote location for analysis.

The data acquisition device is built around a single chip microprocessor. The device requires two inputs during operation. A plurality of vibration sensors are positioned at designated locations along the rotating shaft and provide an analog signal representing the amplitude of vibration. A shaft reference provides a once per revolution shaft reference signal from which the phase angle of vibration can be measured.

An interrupt controller effectively controls the data acquisition process. The shaft reference signals enter the interrupt controller along with a number of other interrupts. The interrupt controller latches each of the interrupts until dealt with by the microprocessor.

Upon receiving the shaft reference signal, the microprocessor suspends all other operations to actuate an analog multiplexer. Input signals from the vibration sensors enter the analog multiplexer, are fed by the multiplexer to an analog to digital converter and are there converted into a binary code by an analog to digital converter. At the same time, the microprocessor uses the shaft reference signal to compute the proper time interval for taking data between shaft reference signals. The microprocessor sets up a programmable timer which successively counts down, each time producing an elapsed time signal which is also latched by the interrupt controller. Each time an elapsed time signal is received, the microprocessor again actuates the multiplexer. Again, input signals from each vibration sensor will enter the multiplexer and will be converted into binary code by the analog to digital converter.

The above process is repeated continuously so long as the shaft reference signal continues to appear periodically. The acquired data is processed by the microprocessor to extract the desired amplitude and angle of the vibration signal from each of the vibration sensors.

In one embodiment, the data sets are transmitted via a telephone modem to a remote location for analysis. Also, real time data can be transmitted to provide means for monitoring the operation of the machinery remotely.

It is the primary object of the present invention to provide a data acquisition device for use in connection with a balancing of large rotating machinery having the capability to acquire data on multiple input channels essentially simultaneously.

Another object of the present invention is to provide a data acquisition device in which the acquired data can be transmitted to a remote location to be analyzed.

Another object of the present invention is to provide a data acquisition device in which the data acquired is processed and displayed in a form that can be readily understood by the operator.

Another object of the present invention is to provide a data acquisition device having editing capabilities such that identifying indicia, notes and other useful information can be stored and displayed along with the acquired data.

Another object of the present invention is to provide a data acquisition device having an automatically switched internal power source for vibration sensors that require power.

Another object of the present invention is to provide a data acquisition device having a printer/plotter wherein acquired data can be printed along with any identifying indicia or notes entered by the operator.

Another object of the present invention is to provide a data acquisition device having the capability to produce a frequency profile of the vibration signal on any selected input channel which is output as a plot on the printer/plotter.

Another object of the present invention is to provide a data acquisition device having the capability to produce a time domain plot of the vibration signal on any selected input channel which is output as a plot on the printer/plotter.

Another object of the present invention is to provide a data acquisition device wherein a variety of vibration sensors can be used during the data acquisition process.

Another object of the present invention is to provide a data acquisition device in which all displayed, saved or printed data is corrected for the anomalies of the particular vibration sensors used so that all data is directly comparable.

Other objects and advantages of the present invention will become apparent and obvious from a study of the following description and the accompanying drawings which are merely illustrative of such invention.

DETAILED DESCRIPTION OF THE INVENTION

Figure 1:
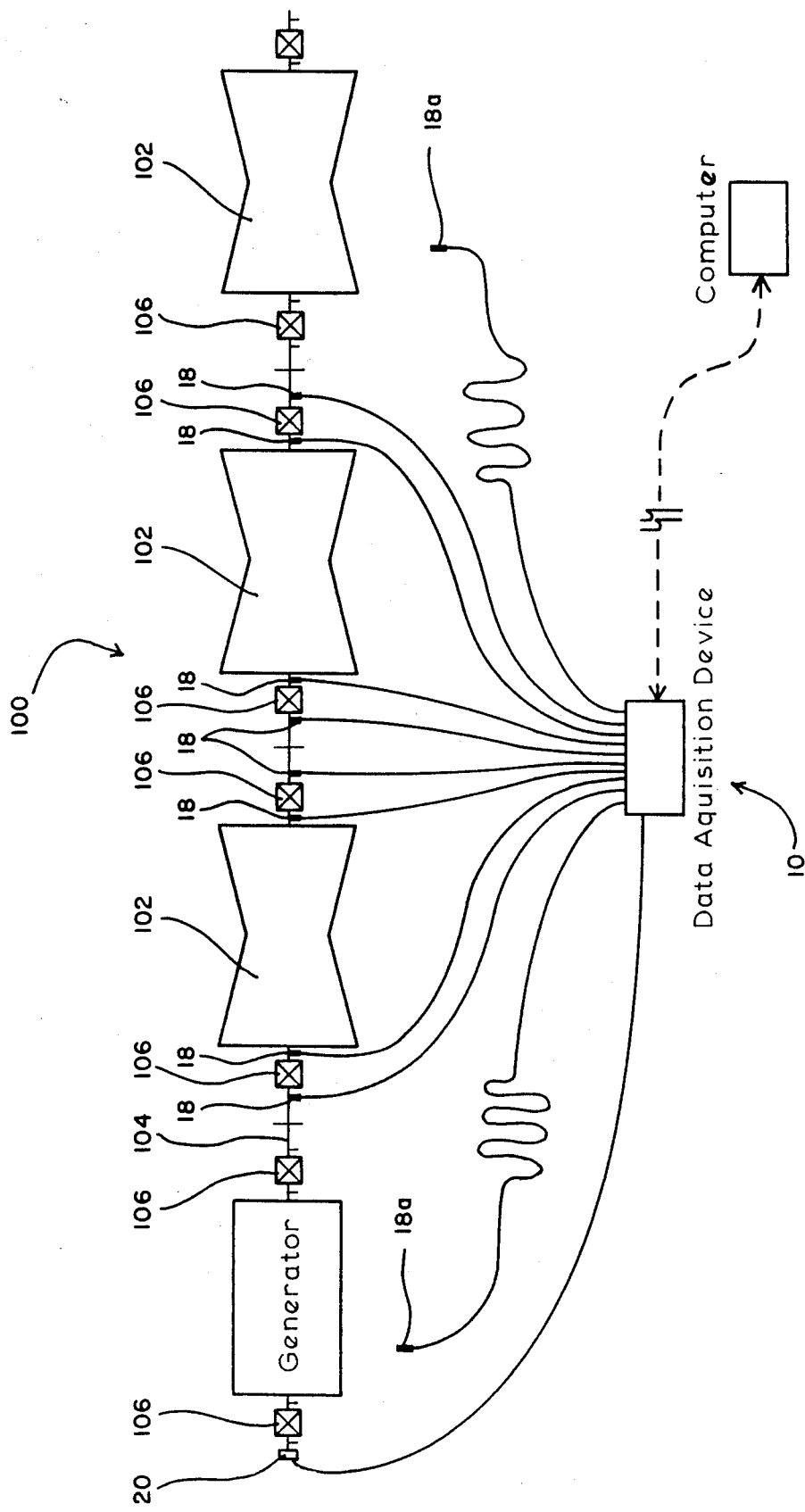
FIG. 1 is a schematic diagram of the data acquisition device being applied to measure vibration in a turbine generator.
Figure 2:
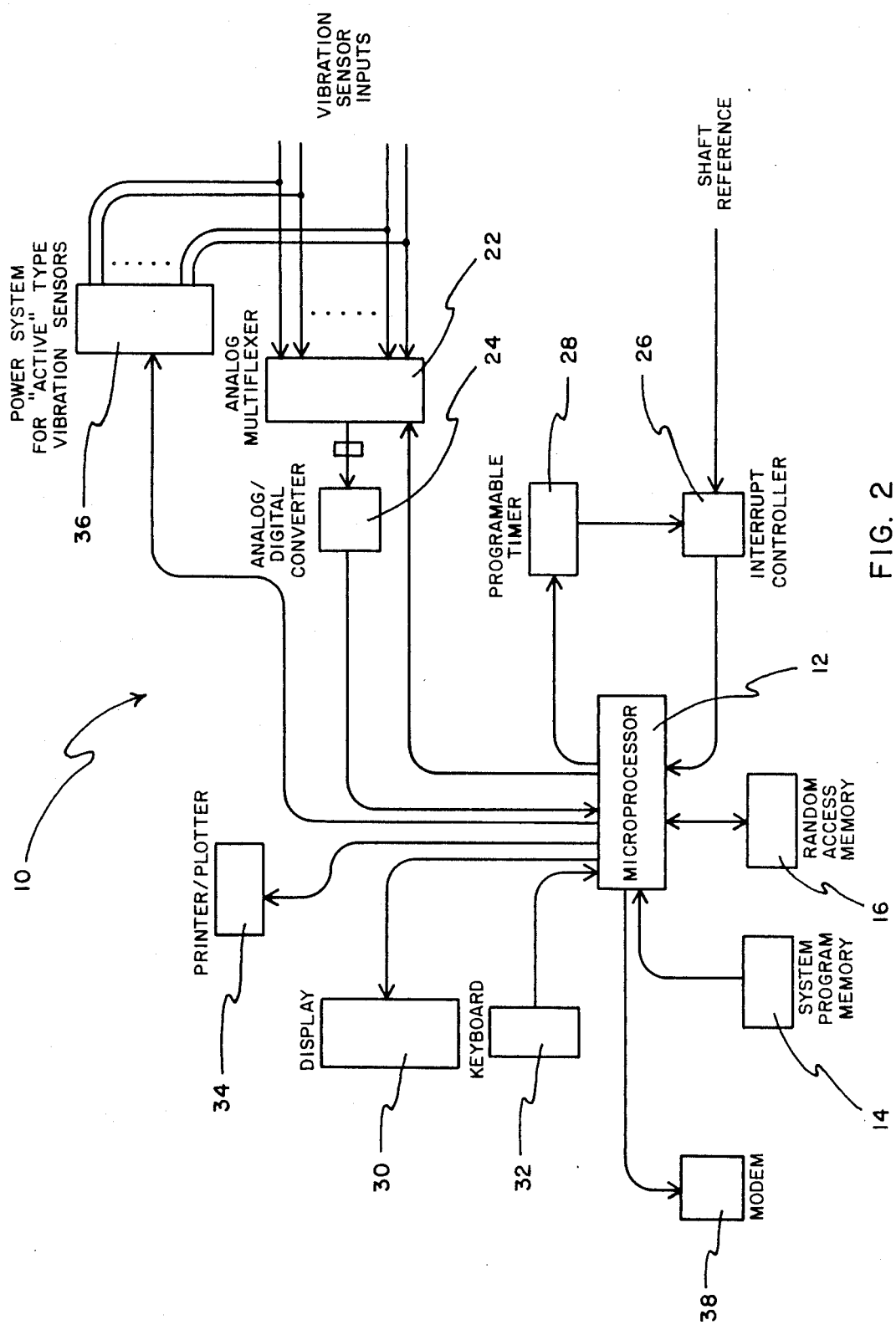
FIG. 2 is a block diagram of the data acquisition device.
Figure 3:
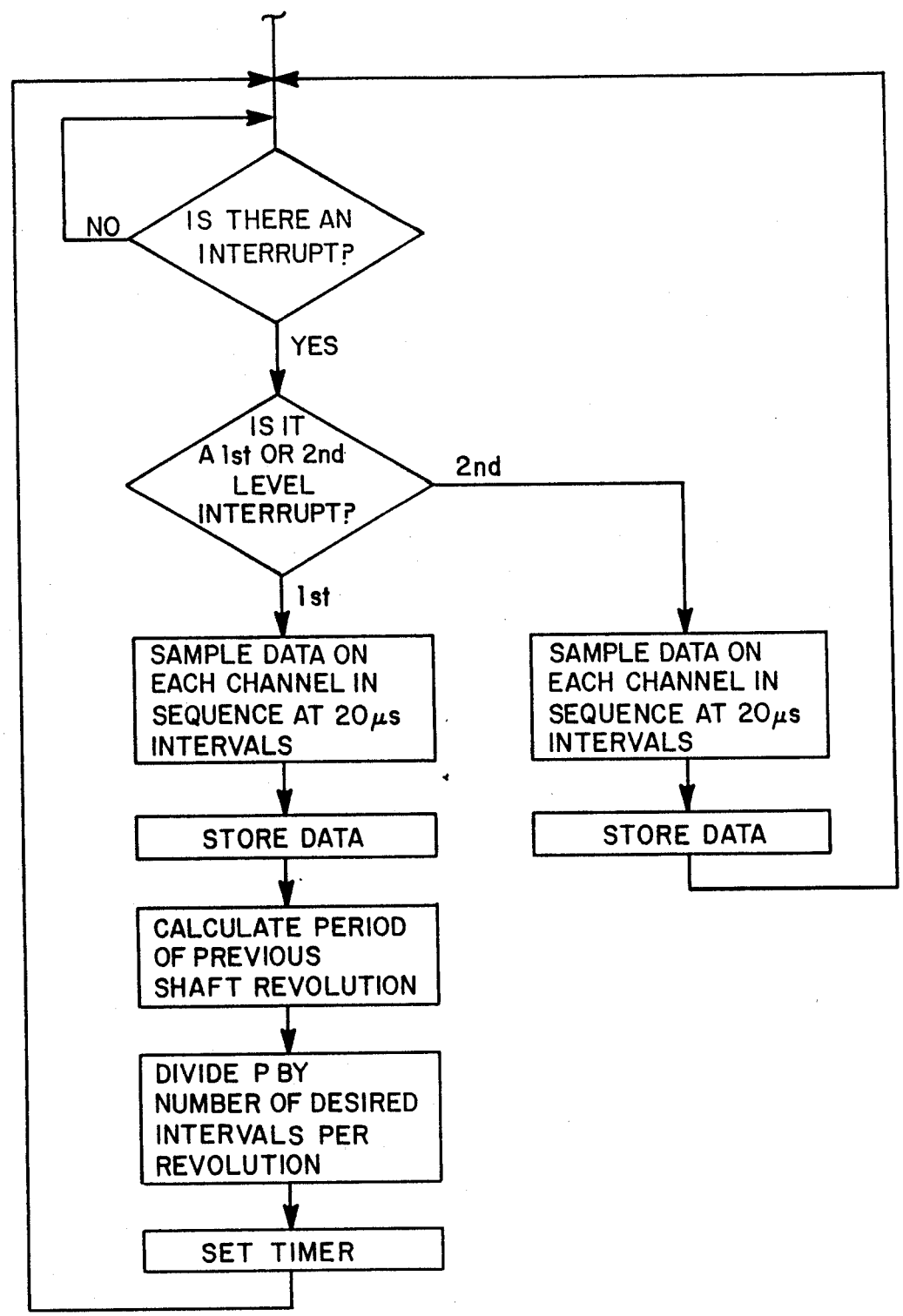
FIG. 3 is a flow diagram showing the operation of the vibration monitoring apparatus.

Referring now to the drawings, the data acquisition device of the present invention is shown therein and indicated generally by the numeral 10. The data acquisition device is used to measure vibration in large rotating machinery, such as gas and steam turbine generators. In FIG. 1, the data acquisition device 10 is shown being used to measure vibration in a turbine generator indicated generally at 100. The turbine generator includes a plurality of turbines 102 mounted on a rotating shaft 104 supported by bearings 106.

Generators of the type shown are influenced by a variety of factors which can cause vibration, chief among them being unbalance in its rotating components. The data acquisition device is particularly adapted to acquire accurate and adequate amounts of data in relatively short periods to analyze vibration problems resulting from unbalance.

In broad terms, the data acquisition device 10 collects data at a plurality of locations along the rotating shaft 104 which is processed and displayed in the form of data sets giving the amplitude and phase of vibration at each location. The distinguishing characteristics of the present invention is that it has the capability to acquire data on a plurality of input channels simultaneously. In other words, the data acquisition 10 acquires data on all input channels during every shaft revolution. Thus, if twelve input channels are used and data is collected 20 times per revolution, the data acquisition device 10 would receive 240 separate input signals per revolution.

The data acquisition device 10 is built around a single-chip microprocessor 12. The embodiment disclosed employs a MOTOROLA MC68000L8 16-bit microprocessor, though any of a number of commercially available microprocessors can be used. The microprocessor runs a systems program stored in system program memory 14. Data acquired during operation is stored in random access memory (RAM) 16.

During operation, the data acquisition device 10 requires input from only two sources. Vibration sensors or pickups 18 are mounted so as to sense the vibration of the rotating shaft 104 or other machinery components of interest. Roving or hand-held sensors 18 can be used if necessary. The data acquisition device 10 will operate with a variety of vibration sensor types including velocity, acceleration and displacement type pick-ups. During the processing stage, the data is automatically corrected for the anomalies of the sensors so that all data is directly comparable. Each of the vibration sensors produces an analog signal, such as a voltage which represents the amplitude and phase of vibration. These input signals from the vibration sensors 18 enter an analog multiplexer 22, each on a separate input channel. Each is in turn fed to the analog to digital converter under microprocessor control and converted into a binary code by the analog to digital converter 24 before entering an input port of microprocessor 12.

The second input source required during operation of the data acquisition device is a shaft reference indicated at 20. (FIG. 1) As with vibration sensors 18, the data acquisition device 10 will accomodate a wide range of shaft references 20, including mechanical and optical references. The purpose of the shaft reference 20 is to provide an arbitrary reference from which the phase angle of vibration can be measured. The reference is established by a once per revolution shaft reference signal produced by the shaft reference 20.

The shaft reference signal is one of a number of interrupts which enters an interrupt controller 26. All interrupts entering into the interrupt controller 26 are assigned a priority value, with the shaft reference constituting a first level interrupt. A programmable timer 28 functioning as an elapsed time counter provides a second level interrupt. The programmable timer is set up by the microprocessor 12 and successively counts down providing an elapsed time signal at predetermined intervals. The significance of the shaft reference signal and elapsed time signal to the data acquisition process will become apparent from subsequent portions of this specification.

Referring again to the vibration sensors 18, it is appreciated that some vibration sensors 18 require power during operation. The data acquisition 10 disclosed incorporates an internal power source 36 controlled by the microprocessor 12 for powering these types of vibration sensors. The embodiment disclosed employs a SILICONIX DG221. The operator simply inputs the type of vibration sensor 18 being used on each channel, and the microprocessor under software control automatically switches the power source 36 for that input channel on or off as required by that pick-up type.

Once the data acquisition device 10 is initialized by entering the type of vibration sensor being used on each input channel, the data acquisition is ready for the acquisition of data. As indicated above, the data acquisition device of the present invention acquires data essentially simultaneously on all input channels then being used. This simultaneous data acquisition process is effectively controlled by the interrupt controller 26, but is initiated by the shaft reference 20. As discussed above, the shaft reference produces a first level interrupt or save reference signal which is latched by the interrupt controller 26. The interrupt controller holds the signal until it is dealt with by the microprocessor 12. Upon receipt of the shaft reference signal, the microprocessor 12 initiates operation of the analog multiplexer 22 and the analog to digital converter. All other operations are suspended. The input signals from each vibration sensor 18 enter the multiplexer 22, each on a separate input channel, and are converted into binary code by an analog to digital converter 24 before entering an input port of microprocessor 12. The analog to digital converter 24 converts the analog signal at a rate of approximately one per twenty microseconds, a delay which is accounted for by the microprocessor 12 during the processing of the data. Adjustment for this delay makes the data acquisition process appear completely simultaneous for all twelve signal inputs. The data entering microprocessor 12 is stored in random access memory 16.

The microprocessor 12 also uses the shaft reference signal to compute a time interval for taking data between shaft reference signals. The shaft reference indentifies only the first point at which data is to be taken. Thus, it is necessary to somehow indicate to the microprocessor 12 when to take data in order to take multiple readings per revolution on each input channel.

This is accomplished by measuring the time between the two previous shaft reference signals and dividing the number of desired time intervals to arrive at a time interval for taking data. After calculating this time interval, the microprocessor 12 sets up the programmable timer 28 which functions as an elapsed time counter. Timer 28 successively counts down, each time producing an elapsed time signal, or second level interrupt. The elapsed time signal is latched by the interrupt controller 26 until dealt with by the microprocessor 12. In reponse to each time elapsed time signal, the microprocessor 12 actuates the multiplexer 22 to cause data to be taken on all input channels. As before, this data is converted into binary code by the analog to digital converter 24, and stored in random access memory 16.

The programmable timer 28 continues to count down successively until another shaft reference signal is received which causes the microprocessor 12 to suspend all operations. In response to the shaft reference signal, the microprocessor 12 again actuates the multiplexer 22 and resets the programmable timer 28. The data acquisition process continues in this manner until terminated by the operator. Multiple shaft revolutions are generally needed to obtain adequate amounts of data for analyzing vibration problems.

Because of the amount of data obtained, it is desirable to simplify the raw data to a more manageable form. The present invention processes the data to create data sets which represent the amplitude and phase angle of the vibration at each location.

The first step in the data processing stage is to compute the amplitude and phase angle of vibration at each location for-each shaft revolution. As will be recalled, the data acquisition device 10 collects data multiple times on each input channel per revolution. This data is used to compute the amplitude and phase angle of vibration. The computational process is based on commonly known digital filtering techniques as described in applicable literature. As required by filtering theory, a specific amount of data (and thus time to acquire this data) is required to complete the amplitude and phase angle. The amount of data required is determined by the desired filter characteristics. Under some operating conditions, the time to acquire the block of data necessary for a new amplitude/angle composition having the preferred filtering characteristics slows the rate at which new amplitude/angle data can be displayed for the operator. This makes it more difficult for the operator to follow trends in a rapidly changing vibration signal. Such a condition can be encountered when using roving or hand-held sensors or when the speed of the turbine-generator is changing rapidly.

To increase the rate at which new data blocks are available for amplitude/angle computation, the present invention employs a technique that puts the acquired data into multiple data blocks in parallel. These data blocks are all the same size, but their beginnings and endings are staggered so that completed data blocks with the most recent data are available more frequently for computation of the amplitude and angle of the vibration signals. For example, if four parallel data blocks are used, then the starting and ending points of each successive data block will be delayed by one fourth the total number of data samples taken for each vibration sensor. As a result, newly completed data blocks will be available for use in computations four times as frequently as if a single data block were used. Each data block contains data for all twelve vibration sensors.

The data processing occurs throughout the data acquisition process during any quiescent period in which the microprocessor 12 is not engaged in the data acquisition process. It is appreciated, however, that all data processing could be performed entirely subsequently to the data acquisition process.

The data collected using the data acquisition device is displayed in the form of data sets representing the amplitude and phase angle of vibration measured at each vibration sensor. The display 30 is incorporated into the body of the data acquisition device 10. In the preferred embodiment, the data acquisition device 10 has data identification capabilities. Using a keyboard 32, the operator enters information, such as job identification, location of each vibration sensor, time, data and any other information. This information is displayed with the data sets and thus eliminates the need for keeping separate detailed notes.

The data acquisition device also incorporates an internal printer/plotter 34 for producing a hard record of data. The printer/plotter 34 has multiple modes of operation. In the print mode, data is printed out along with the current time and data, and if entered, any identification and/or notes entered by the operator. In the frequency scan mode, the printer/plotter produces a frequency profile of the vibration signal on any selected input channel. In the wave plot mode, a time domain plot of the vibration signal on the selected input channel is produced.

In the preferred embodiment the data acquisition device 10 incorporates a telephone modem 38 for transmitting data to a remote location where a sophisticated computer is available for analyzing vibration problems. The data can be transmitted as data sets or as real time data which facilitates constant monitoring of vibration over extended periods of time.

The present invention may, of course, be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A data acquisition device for collecting data concerning vibration of a rotating component which rotates through a cycle, said data acquisitiond device being operable over a plurality of cycles, and responsive to changes in angular velocity of the rotating component, comprising:
    (a) means for generating a first periodic interrupt signal which occurs at least once per cycle;
    (b) means for dividing the period of each cycle of the rotating component into a plurality of equal time increments selected by a user, said dividing means including adjustment means for varying said time increments from cycle to cycle depending upon changes in the angular velocity of the rotating component;

(c) means for generating a second periodic interrupt signal for each time increment of each cycle;

(d) a plurality of vibration sensors mounted at spaced locations on the rotating component for detecting vibrations in the rotating component and producing an output signal representative of the vibration at the location of the sensors, wherein vibrations are monitored at a plurality of said locations simultaneously;

(e) a signal processor having a plurality of input channels for receiving output signals from respective vibration sensors;

(f) input means forming a part of the signal processor and responsive to the first and second periodic interrupt signals for receiving output signals from a plurality of the vibration sensors in response to each such periodic interrupt signal; and (g) means for digitizing and storing said output signals for subsequent processing.

2. The data acquisition device accoding to claim 1, wherein the means for varying said time increments includes means for measuring the period of the cycle preceding the current cycle and dividing said period by the selected number of time increments for the current cycle.

3. A method for collecting data relating to vibrations of a rotating component which rotates throug a cycle comprising:

(a) generating a first periodic interrupt signal at least once per cycle;

(b) dividing each cycle of the rotating component into a plurality of equal time increments;

(c) varying the time increments from cycle to cycle depending upon changes in angular velocity of the rotating component;

(d) generating a second periodic interrupt signal for each time increment of each cycle;

(e) mounting a plurality of vibration sensors at different locations along the rotating component fo detecting vibration and producing an output signal representative of the vibration at the locations of the sensors;

(f) monitoring the vibration of the rotating component at a plurality of said locations simultaneously;

(g) transmitting output signals from a plurality of the vibration sensors to a signal processor in response to each interrupt signal; and (h) storing the output signals in a memory device in the signal processor.

4. The method according to claim 3, wherein the step of varying the time increment from cycle to cycle includes: measuring a period of the cycle preceding a current cycle; and dividing said period by a desired number of increments for the current cycle.

5. A data acquisition device for collecting data concerning vibration of a rotating component which rotates through a cycle, said data acquisition device being operable over a plurality of cycles and responsive to changes in angular velocity of the rotating component, comprising:

(a) menas for dividing a period of eahc cycle into a plurality of equal time increments and producing a periodic interrupt signal at completion of each such time increment;

(b) means for adjusting the time increment from cycle to cycle depending upon changes in the angular velocity of the rotating component, said adjustment means including:

(1) means for determining the period of each cycle; and (2) means for dividing the period of a most recently completed cycle by a selected number of increments to establish a time interval for the next cycle;

(c) a plurality of vibration sensors moutned at spaced locations on the rotating component for detecting vibrations in the rotating component and producing an output signal representative of the vibration at the location of the sensors, wherein vibrations are monitored at a plurality of said locations simultaneously;

(d) a signal processor having a plurality of input channels for receiving output signals from respective vibration sensors;

(e) input means forming a part of the signal processor and responsive to the periodic interrupt signal for receiving output signals from a plurality of the vibration sensors in response to each such interrupt signal; and (f) means for digitizing and storing said output signals for subsequent processing.

* * * * *